United States Patent
Schätzle et al.

(10) Patent No.: US 6,264,608 B1
(45) Date of Patent: Jul. 24, 2001

(54) ACOUSTIC THERAPY APPARATUS COMPRISING A SOURCE OF THERAPEUTIC ACOUSTIC WAVES AND AN ULTRASOUND LOCATING MEANS

(75) Inventors: Ulrich Schätzle, Roettenbach; Erhard Schmidt, Erlangen; Bernhard Thum, Koetz, all of (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 09/155,491
(22) PCT Filed: Mar. 27, 1997
(86) PCT No.: PCT/DE97/00632
§ 371 Date: Jan. 19, 1999
§ 102(e) Date: Jan. 19, 1999
(87) PCT Pub. No.: WO97/36650
PCT Pub. Date: Oct. 9, 1997

(30) Foreign Application Priority Data

Apr. 2, 1996 (DE) .............................................. 196 13 243

(51) Int. Cl.$^7$ ...................................................... A61B 8/00
(52) U.S. Cl. ........................... 600/439; 600/443; 600/466; 600/467; 600/472; 601/2; 601/3; 607/122; 607/88; 607/92; 607/96; 607/97
(58) Field of Search .................................. 600/407, 437, 600/439, 443, 466, 467, 472; 601/2, 3; 607/122, 88, 92, 96, 97

(56) References Cited

U.S. PATENT DOCUMENTS

| | | | |
|---|---|---|---|
| 4,917,097 | * 4/1990 | Proudian et al. | 128/662.06 |
| 5,373,845 | * 12/1994 | Gardineer et al. | 128/660.09 |
| 5,471,988 | * 12/1995 | Fujio et al. | 128/660.03 |
| 5,474,071 | 12/1995 | Chapelon et al. | |
| 5,588,432 | * 12/1996 | Crowley | 128/660.03 |
| 5,817,021 | * 10/1998 | Reichenberger | 600/439 |

FOREIGN PATENT DOCUMENTS

| | | |
|---|---|---|
| 0 668 052 | 8/1995 | (EP) . |
| WO 93/16641 | 9/1993 | (WO) . |
| WO 95/02994 | 2/1995 | (WO) . |
| WO 95/19143 | 7/1995 | (WO) . |

* cited by examiner

*Primary Examiner*—Peter Vo
*Assistant Examiner*—Jeoyuh Lin
(74) *Attorney, Agent, or Firm*—Schiff Hardin & Waite

(57) ABSTRACT

An acoustic therapy apparatus has a source of therapeutic acoustic waves and an ultrasound locating means with an ultrasound transducer, wherein the source and the ultrasound transducer are combined to form an oblong applicator with a longitudinal axis provided for introduction into the body interior of a patient, the ultrasound locating system generating ultrasound images with respect to a plane that contains the longitudinal axis of the applicator. The source and the ultrasound transducer are disposed relative to each other in the applicator so that the source and the ultrasound transducer are successively arranged in the direction of the longitudinal axis, with the ultrasound transducer being arranged preceding the source the in introduction direction, and the center axis of the plane describing an angle of less than 90° with that section of the longitudinal axis of the applicator located in the region of the source so that the center axis is inclined toward the source.

5 Claims, 4 Drawing Sheets

ACOUSTIC THERAPY APPARATUS COMPRISING A SOURCE OF THERAPEUTIC ACOUSTIC WAVES AND AN ULTRASOUND LOCATING MEANS

BACKGROUND OF THE INVENTION

1. Field of the Invention

The invention is directed to an acoustic therapy apparatus of the type having a source of therapeutic acoustic waves and an ultrasound locating means with an ultrasound transducer, the source and the ultrasound transducer are combined to form an oblong applicator with a longitudinal axis adapted for introduction into the body interior of a patient with the source and the ultrasound transducer being successively arranged in the direction of the longitudinal axis, so that ultrasound images with respect to a circular sector-shaped plane of section that contains the longitudinal axis of the applicator and whose center axis is the angle bisector of the plane of section can be generated with the ultrasound locating means.

2. Description of the Prior Art

In order to be able to obtain a good image of a region that is to be treated with therapeutic acoustic waves using an ultrasound locating means in a conventional therapy apparatus of the type initially described, the source of therapeutic acoustic waves is subdivided into two sections of equal length between which the sector scanner is located. The sector scanner in usually contains a small linear array that is operated in as a phased array. A sector scanner containing a linear array is employed, because the slight installation space required for such a sector scanner makes it possible to arrange the two sections of the source of therapeutic acoustic waves in close proximity, which is beneficial for acoustic reasons. Moreover, the slight installation space required for such a sector scanner has a beneficial effect on the dimensions of the applicator, so that a use of the applicator is also possible under constricted space conditions, for example endoluminal application (use in body cavities).

U.S. Pat. No. 5,474,071 discloses a therapy apparatus of the type initially described wherein the source of therapeutic acoustic waves and the ultrasound transducer are arranged following one another in the direction of the longitudinal axis, with which ultrasound images with respect to a planar of section (slice) that contains the longitudinal axis of the applicator can be generated with the ultrasound locating means, with the center axis of the plane of section describes an angle of less than 90° with the longitudinal axis of the planar section so that the center axis is inclined toward the source. In this way, it is possible to always image the entire region to be treated with the therapeutic acoustic waves in the ultrasound image generated with the ultrasound locating means without requiring a subdivision of the source of therapeutic acoustic waves into two sections. However, extremely little installation space is available for the ultrasound transducer.

SUMMARY OF THE INVENTION

An object of the present invention to provide a therapy apparatus of the type initially described wherein, without dividing the source of therapeutic acoustic waves into two sections, it is possible to produce a good image of the region to be treated with the ultrasound locating means while still providing adequate installation space for the ultrasound transducer.

This object is inventively achieved in a therapy apparatus wherein the ultrasound transducer is arranged preceding the source in the introduction direction, and wherein, proceeding from a position in which the center axis of the planar section describes an angle of less than 90° with the section of the longitudinal axis of the applicator located in the region of the source, so that the center axis is inclined toward the source and is adjustable such that it describes an angle greater than 90° with that section of the longitudinal axis of the applicator located in the region of the source. It is thus clear that the sector scanner is arranged at the distal end of the applicator, with the result that adequate installation space is available for the sector scanner. As a result of the slant of the center axis of the planar section, it is nonetheless possible to always image the entire region to be treated with the therapeutic acoustic waves in the ultrasound image generated with the ultrasound locating means.

It is also possible to image the body region of the patient located in the region of the distal end of the applicator, in particular in front of the distal end, during the introduction of the applicator into a patient with the ultrasound locating means, in order to obtain information that make it possible to recognize whether an unproblematical introduction is possible or whether, for example, the introduction direction must be corrected. For this purpose, in an embodiment of the invention the center axis of the plane of section is adjustable such that it describes an angle greater than 90° with that section of the longitudinal axis of the applicator located in the region of the source.

Even given employment of a mechanical sector scanner, the inventive structure, with little technical outlay, makes it advantageously possible to design the applicator with dimensions so that it is introducible into the body interior of a human patient along natural paths.

The arrangement of the ultrasound transducer preceding the source in the sense of the introduction direction, i.e. at the distal end of the applicator, offers the advantage that the ultrasound locating means also supplies a good image under all conditions given endoluminar application.

DESCRIPTION OF THE PREFERRED EMBODIMENTS

The inventive acoustic therapy apparatus has a therapeutic acoustic wave source 1 and an ultrasound locating system with a mechanical sector scanner 2.

Figure 1:
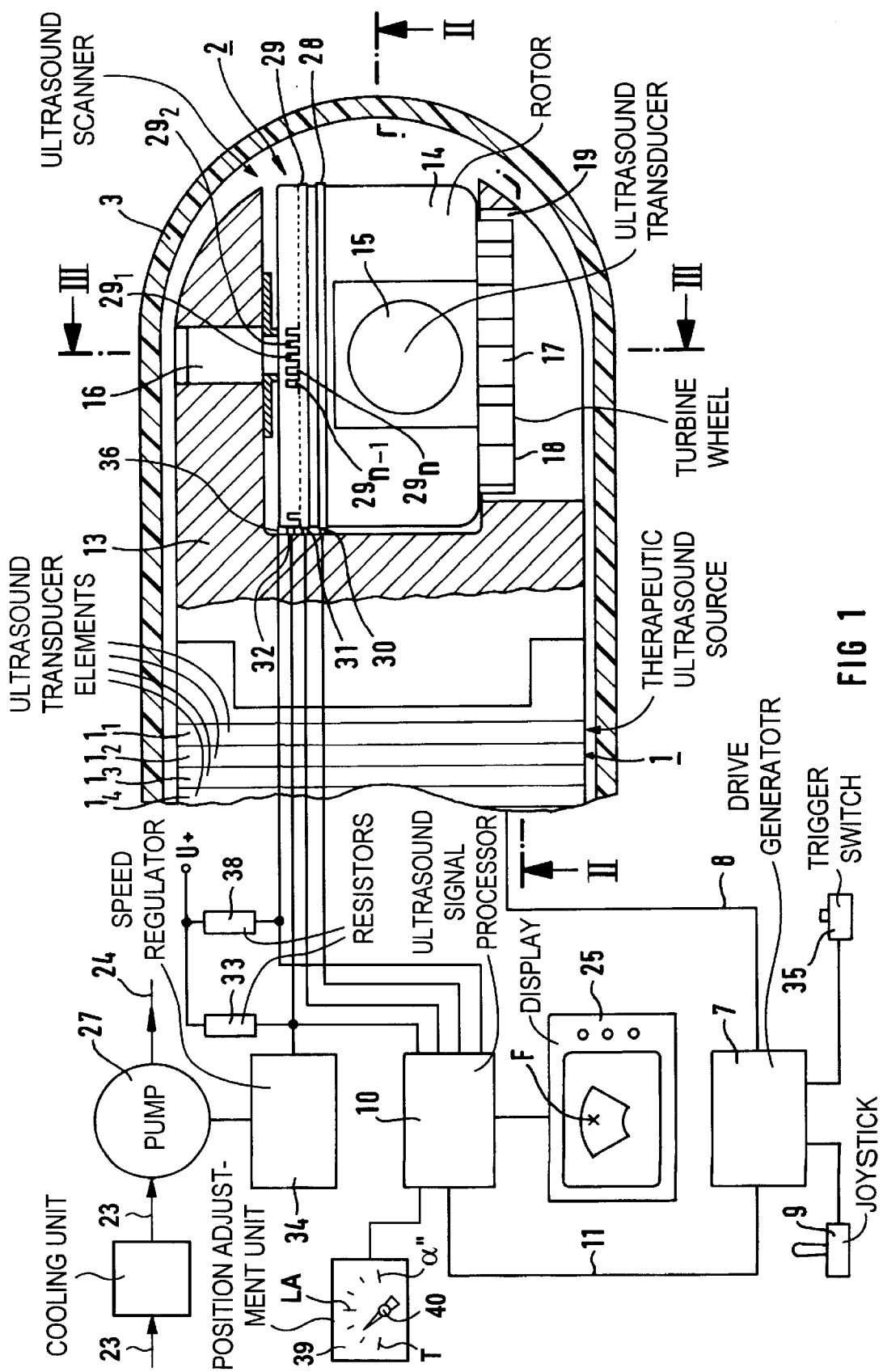
FIG. 1 is a longitudinal section through a portion of an inventive therapy apparatus, also showing components for operating the therapy apparatus and for operating an ultrasound apparatus embodied in the therapy apparatus.
Figure 2:
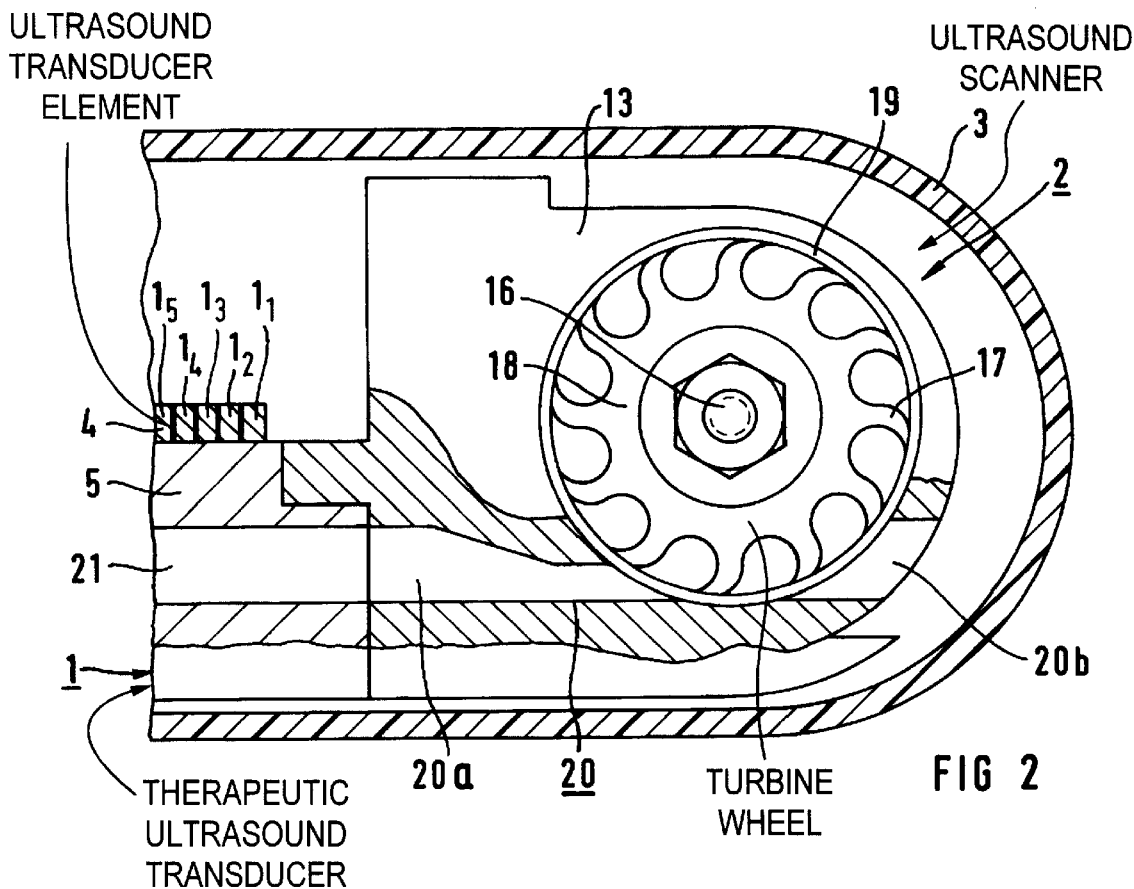
FIG. 2 is a sectional view taken along line II—II of FIG. 1.

As can be seen from FIGS. 1 and 2, the therapeutic acoustic wave source 1 and the sector scanner 2 are combined to form an oblong applicator. The applicator has a tubular housing 3 fashioned dome-shaped at its distal end, i.e. its end provided for introduction into a body opening, preferably a natural body orifice. The housing is formed of a material highly permeable for ultrasound waves, for example of plastic, for example polymethylpentene (TPX®).

In a way that is not shown, the interior of the applicator, i.e., the interior, of the housing 3 is filled with a liquid suitable as a propagation medium for ultrasound, for example light mineral oil.

Figure 5:
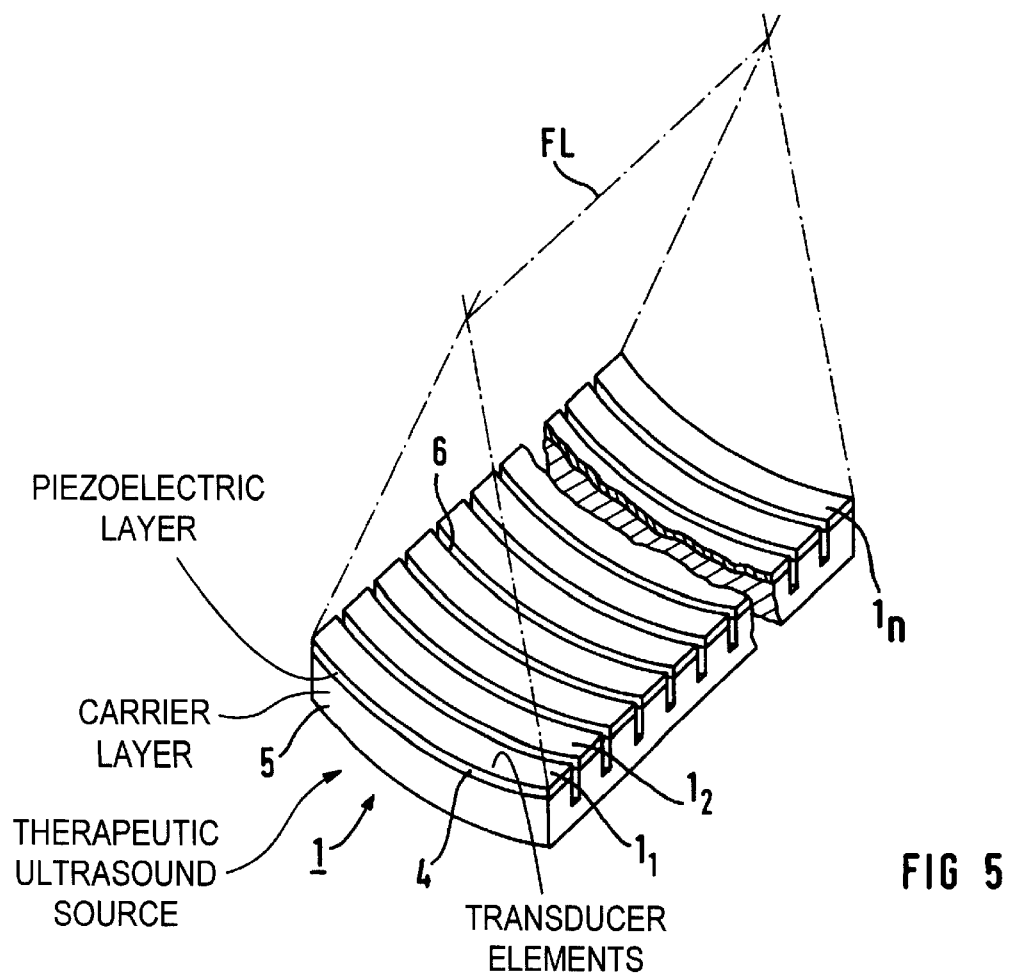
FIG. 5 shows the therapeutic ultrasound wave source in the therapy apparatus of FIG. 1, in a perspective view.

The source 1 is of an elongated piezoelectric source that, according to FIG. 5, is constructed as a linear array and emits ultrasound waves during the treatment of a patient with the therapy apparatus.

Accordingly, the source 1 is subdivided into a number of ultrasound transducer elements $1_1$, $1_2$, etc., through $1_n$. The subdivision is implemented such that it is possible to individually drive each of the ultrasound transducer elements $1_1$ through $1_n$ to generate ultrasound waves by supplying a suitable electrical signal. For clarity, the source 1 is shown shortened in FIG. 5 (which is not to scale), so that only a few, namely approximately 10 ultrasound transducer elements are shown. In practice, the source 1 is subdivided into, for example, 128, 192 or 256 ultrasound transducer elements and exhibits a length of a few centimeters.

The source 1 is constructed in a known way such that the actual piezoelectric material 4 is applied in the form of a layer having constant thickness onto a carrying member 5 with suitable acoustic impedance and, likewise, constant thickness. In a way that is not shown, the connection of the layer 4 of piezoelectric material with the carrying member 5 ensues with a metallic layer whose thickness is small compared to that of the layer 4. That surface of the piezoelectric layer 4 facing away from the carrying member 5 is likewise provided with a thin metallic layer (not shown).

These metallic layers serve as electrodes for the electrical contacting of the ultrasound transducer elements $1_1$ through $1_n$.

In order to obtain ultrasound transducer elements $1_1$ through $1_n$ that can be driven independently of one another, the piezoelectric layer 4 connected to the carrying member 5 is subdivided into the individual ultrasound transducer elements $1_1$ through $1_n$ by narrow incisions proceeding transversely to the longitudinal axis of the source 1, one thereof being referenced 6 in FIG. 5.

In order to mechanically decouple the ultrasound transducer elements $1_1$ through $1_n$ from one another, the incisions 6 has a depth that is clearly greater than the thickness of the piezoelectric layer 4.

Given suitable drive of the individual ultrasound transducer elements $1_1$ through $1_n$, it is possible to focus the ultrasound waves emitted by the source 1 onto a focus zone and to displace the focus zone of the ultrasound waves. As is known in an array of this type focussing, and thus the implementation of a scan motion can occur only in the direction of the longitudinal axis of the linear array as well as in a direction of the sound propagation orthogonal to the surface of the ultrasound transducer 5. In order to also achieve a focussing transversely thereto, the ultrasound transducer 5 is cylindrically curved around an axis proceeding parallel to its longitudinal axis in the known way indicated in FIG. 5, so that, given simultaneous drive of all ultrasound transducer elements $1_1$ through $1_n$, a focussing of the ultrasound waves is produced on a line focus referenced FL in FIG. 5 that proceeds parallel to the longitudinal axis of the linear array.

When, by contrast, the ultrasound transducer elements $1_1$ through $1_n$ are driven with signals that are phase-offset relative to one another in a suitable way, then a focussing ensues onto an approximately ellipsoid focus zone whose center can be displaced within an approximately rectangular zone Z shown in FIG. 5 dependent on the phase offset of the signals supplied to the ultrasound transducer elements $1_1$ through $1_n$. The zone Z is located in the plane that contains the longitudinal axis of the ultrasound transducer 5 as well as the line focus FL.

A drive generator means 7 provided for the drive of the ultrasound transducer elements $1_1$ through $1_n$ is schematically illustrated in FIG. 1 and is in communication with the source 1 via a line 8 that, in practice, is formed by a number of leads equals the number of ultrasound transducer elements.

A joystick 9 is connected to the drive generator 7 in order to be able to displace the focus zone within the zone Z according to the respective requirements.

In addition to the sector scanner 2, the ultrasound locating system which allows the generation of real-time or, to be more precise, quasi real-time ultrasound images, includes a conventionally constructed ultrasound signal processor 10 interacting with the sector scanner 2 that receives a signal corresponding to the respectively set position of the focus of the ultrasound waves from the drive generator 7 via a line 11. On the basis of this signal, the ultrasound signal processor 10 mixes a mark F' that indicates the position of the center F of the focus zone in the ultrasound images generated with the ultrasound locating means into the ultrasound images generated in collaboration with the sector scanner 2.

A cable 12 (see FIG. 6) conducted out of the housing 3 to the exterior includes, the line 8 connecting the drive generator 7 with the ultrasound transducer elements $1_1$ through $1_n$ as well as the lines 10 connecting the sector scanner 2 with the ultrasound signal processor 10.

Figure 6:
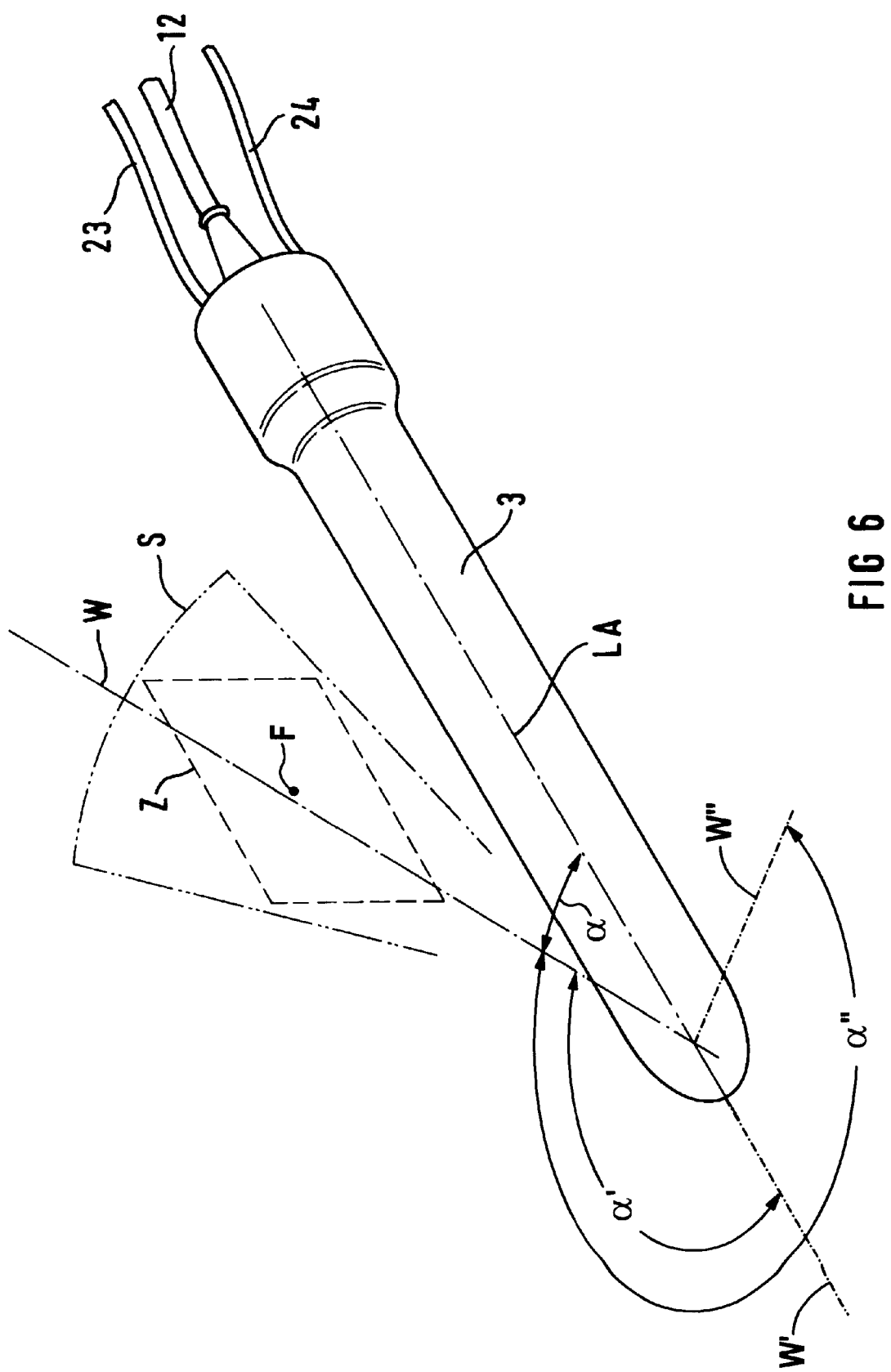
FIG. 6 is a perspective view of the exterior of the ultrasound applicator of the therapy apparatus of FIG. 1.

The source 1 and the sector scanner 2 are arranged following one another in the direction of the longitudinal axis of the applicator such that the sector scanner 2 is arranged at the distal end of the applicator preceding the source 1 in the introduction direction of the applicator, such that, in the way shown in FIG. 6, the center plane of the circular sector-shaped layer S scanned with the sector scanner 2 lies in the plane containing the longitudinal axis of the ultrasound transducer as well as the line focus FL. As mentioned, the focus of the therapeutic ultrasound waves is displaceable in this plane. The angle bisector W of the circular sector-shaped layer S scanned with the sector scanner 2, which is identical to the center axis thereof in the described exemplary embodiment, describes an angle α—in the way shown in FIG. 6—that is less than 90° with that section of the longitudinal axis of the ultrasound transducer 5 situated in the region of the source 1 and, thus, with that section of the longitudinal axis LA of the applicator that is located in the region of the source 1.

Since the angle bisector W of the planar section S describes the angle α with the longitudinal axis LA of the applicator in such a way that the angle bisector W is inclined toward the source 1, the entire region, i.e. the zone Z, in which the center of the focus zone F can be situated is always imaged in the ultrasound image generated with the ultrasound locating system, even though the sector scanner 2 is attached to the distal end of the applicator.

The center of the focus zone for a possible position of the focus zone is shown in FIG. 6 and referenced F.

The described operating mode wherein the angle a is less than 90° and the angle bisector W is inclined toward the source 1 represents the operating mode during the treatment of a patient with the ultrasound waves emitted by the source 1.

However, a second operating mode is possible wherein the angle bisector W of the plane S of section is inclined away from the section of the longitudinal axis LA of the applicator located in the region of the source 1 and the angle between the angle bisector W and section of the longitudinal axis LA located in the region of the source 1 is greater than 90°. This operating mode is indicated in FIG. 6 by means of the angle bisectors W' and W" for two exemplary angles α' and α" being shown dotted. α' and W' thereby illustrate an intermediate position. α" and W" correspond to the one limit position. The other limit position is defined by α and W.

During the introduction of the applicator into a patient, the second operating mode serves the purpose of displaying the body region of the patient located in the region of the distal end of the applicator during the introduction event, particularly in front of the distal end, with the ultrasound locating means in order to obtain information that make it possible to recognize whether an unproblematical introduction is possible or whether, for example, the introduction direction must be corrected.

At the beginning of the introduction of the applicator, a position of the angle bisector of the plane S of section will usually be selected wherein this proceeds at least approximately parallel to the longitudinal axis of the applicator or at least approximately coincides therewith. This situation is illustrated in FIG. 6 by the position of the angle bisector reference W' and by the angle α'. When obstacles occur during the introduction event and when, for other reasons, information are required about the body region of the patient surrounding the distal end of the applicator during the introduction event, the angle bisector between the angles α and α" can be arbitrarily adjusted in order to obtain suitable ultrasound images, whereby α"=360°−2α preferably applies.

Figure 3:
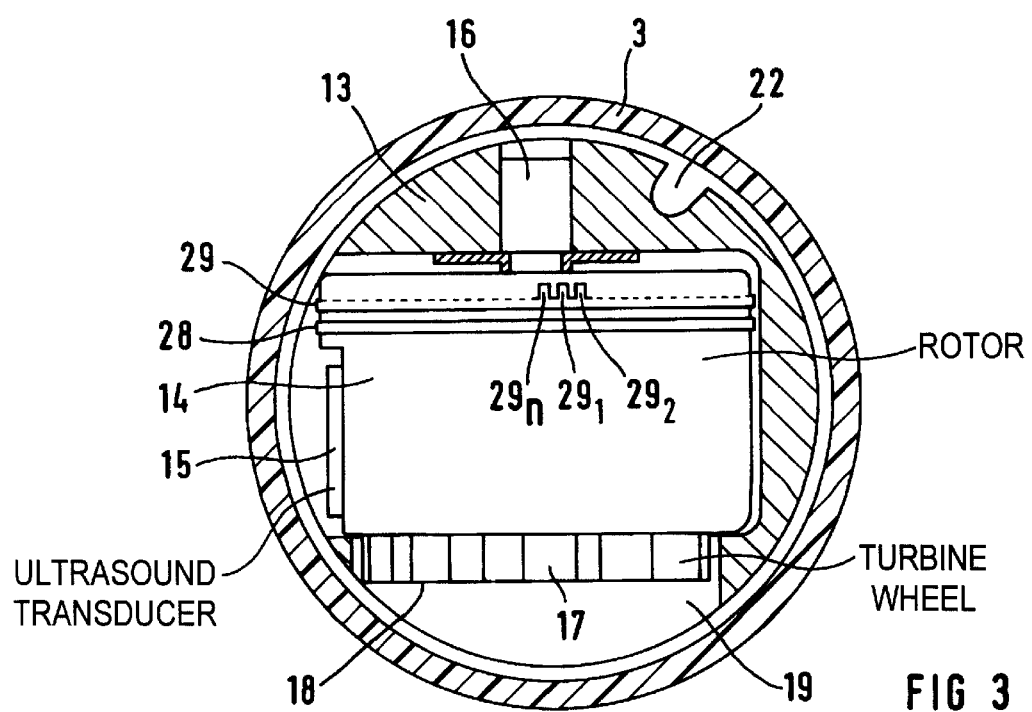
FIG. 3 is a sectional view taken along line III—III of FIG. 1.
Figure 4:
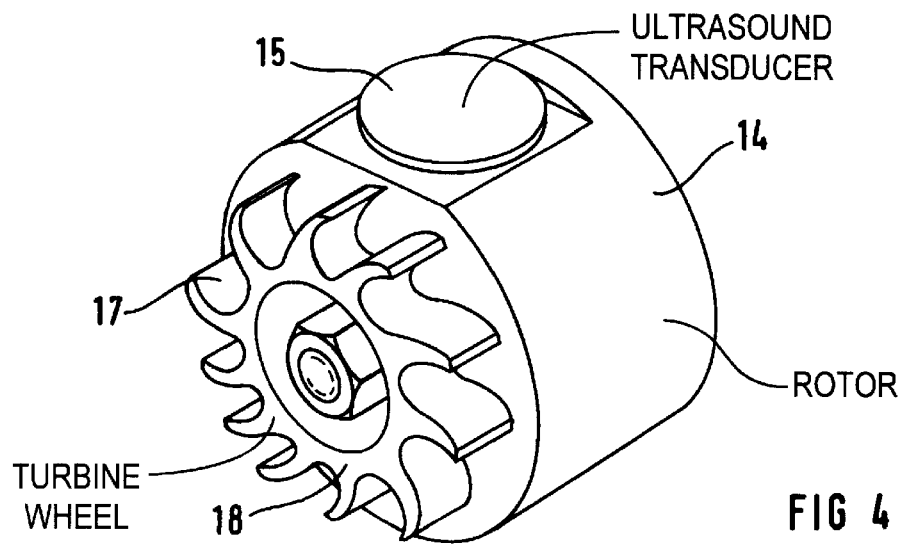
FIG. 4 is a perspective view of a rotor of the sector scanner in the therapy apparatus of FIG. 1.

As can be seen from FIGS. 1 through 3, the sector scanner 2 has a base member 13 whose shape is adapted to the inside contour of the housing 3 and that is provided with a slot-shaped recess in which a rotor 14 to which an ultrasound transducer 15 is attached is accepted.

The rotor 14 is rotatably mounted with a plain bearing (not shown) on a shaft 16 pressed into an opening of the base member 13.

Without interposition of a gearing, the rotor 14 is driven with a pneumatically operated motor, using the mineral oil contained in the ultrasound applicator as a pressure agent.

This motor is constructed in the fashion of a turbine and, has a turbine wheel 18 firmly attached to the rotor 14 and provided with blades 17. The turbine wheel 18 is accepted in an opening 19 of the base member 13 lying opposite the opening accepting the shaft 16, this opening 19 being only slightly larger than the outside diameter of the turbine wheel 18.

A channel 20 extends in the base member 13, the channel 20 being arranged such that the opening 19 divides it into two sections, namely an admission section 20a and a return section 20b, whereby the admission section is arranged such that mineral oil conducted through the channel 20 as a pressure agent acts on the blades 17 of the turbine wheel 18 with a suitable flow direction, tangentially in the case of the described exemplary embodiment, and places it into rotation together with the rotor 14 and the ultrasound transducer 15 into rotation.

The mineral oil is supplied to the admission section 20a via a channel 21 extending through the carrying member 5 of the source 1. in this way, the mineral oil simultaneously serves for cooling the source 1. From the return section 20b, the mineral oil proceeds via a channel 22 provided in the base member 13 to a conduit 23, see FIG. 6. The channel 21 is supplied by a conduit 24 that is likewise shown in FIG. 6. The conduits 23 and 24 form a circulation path in which a pump 27 having controllable pump capacity (pressure or flow-through quantity) is connected. If required, the circulation path can contain a cooling unit 36 for the mineral oil in the way shown in FIG. 1.

As already explained, the ultrasound transducer 15 collaborates with the ultrasound signal processor 10, which is connected to a display 25. The transfer of electrical signals required thereto ensues via wiper rings 28 and 29 as well as wiper contacts 30 and 31, whereby the actual signals proceed via the wiper ring 28 and the wiper contact 30 and the wiper ring 29 together with the wiper contact 31 produce the connection to ground. As mentioned, the corresponding lines proceed in the cable 12.

For the proper generation of ultrasound images, the ultrasound image generating unit 17 also requires a signal with respect to the angular position of the rotor 14. This is generated in that the wiper ring 29 comprises axially directed segments $29_1$ through $29_n$, n=1 through 400, arranged at identical angular spacing from one another that are sensed with a further wiper contact 32 that is connected via a resistor 33 to a positive voltage U+, and a line proceeding in the cable 12 is connected to the ultrasound image generating unit 17. In order to generate a reference signal for a specific angular position of the rotor 14, for example a signal indicating that an angle of 90° is present between the angle bisector and the longitudinal axis of the applicator, one of the sigments is made longer than the others, for example the segment 29, as shown. It is sensed with a wiper contact 37. This, too, is connected via a resistor 38 to the positive voltage U+ and a line 12 proceeding in the cable 12 is connected to the ultrasound image generating unit 17.

The square-wave signal available at the wiper contact 32 is supplied not only to the ultrasound image generating unit 17 but also to a speed regulator 34 constructed using fuzzy logic that controls the pump capacity of the pump 27 for the purpose of a defined, constant angular velocity of the rotor 14, i.e. a constant frequency of the square-wave signal.

In order to be able to set the position of the angle bisector of the planar section S, an adjustment unit 39 that has an adjustment knob 40 with which the angle bisector can be brought into the position (W, α) corresponding to the first operating mode on the basis of a scale is connected to the ultrasound signal processor 10. The corresponding position of the adjustment knob 40 is referenced T on the scale. That position (W', α') of the angle bisector in which this proceeds parallel to the longitudinal axis LA of the applicator corresponds to the position of the adjustment knob 40 referenced LA on the scale. The position (W", α") of the angle bisector opposite the position of the angle bisector present in the first operating mode corresponds to the position of the adjustment knob 40 referenced with α" on the scale.

On the basis of the signals from the wiper contacts 32 and 37, the ultrasound signal processor 10 adjusts the position of the angle bisector of the planar section S corresponding to the setting of the adjustment knob 40 of the adjustment unit 39.

For the implementation of a treatment, the applicator is first introduced into the corresponding body opening, for example the rectum of a male patient. This occurs under ultrasound supervision with the ultrasound locating system initially operating in the second operating mode. The adjustment knob 40 of the adjustment unit 39 is thereby initially set to the position LA. Insofar as necessary, other positions of the angle bisector of the planar section S can also be selected with the adjustment knob 40 during the introduction event. When the introduction event has been ended, the ultrasound locating system is placed into the first operating mode in that the adjustment knob 40 is brought to the position T. With the assistance of the ultrasound locating system and the ultrasound image displayed on the display 25, the applicator is then aligned such that the body region to be treated, for example a benignly enlarged prostate, is located approximately in the center of the ultrasound image. In a way not shown in greater detail, the applicator is then fixed in this position with a stand or the like.

Subsequently, the focus of the ultrasound waves is directed with the joystick 9 onto a region of the prostate to be treated.

When a trigger switch 35 (see FIG. 1), which can, for example, be a foot switch, is actuated, then the source 1 emits an ultrasound pulse whose amplitude and time duration are selected such that the prostate tissue located in the focus of the ultrasound waves is heated to such high temperatures that the cell protein is denaturized and, thus, the affected prostate tissue is necrotize.

The described procedure can now be repeated, potentially automatically, with a respectively slight displacement of the focus of the ultrasound waves until the entire prostate or a specific region of the prostate has been treated.

The structure of the motor operated with pressure agent as a turbine that was described in conjunction with the exemplary embodiment according to FIGS. 1 through 6 is intended as only an example; the motor operated with a pressure agent can alternatively be constructed in some other way, for example as a rotary piston motor.

An ultrasound source is provided as source of therapeutic ultrasound waves in the above-described exemplary embodiment. This can emit ultrasound in the form of ultrasound pulses or in the form of continuous sound as therapeutic acoustic waves. Instead of an ultrasound source, however, some other source of therapeutic acoustic waves can be provided, for example a shock wave source.

In the case of the described exemplary embodiment, a mechanical sector scanner is provided. Instead of this, however, there is also the possibility of providing an electronic sector scanner that contains a phased array, whereby is can be necessary under certain circumstances in this case to pivotably arrange the phased array insofar as the electrically realizable range of swivel of the angle bisector or, center axis of the planar section S is not adequate.

Although other modifications and changes may be suggested by those skilled in the art, it is the intention of the inventors to embody within the patent warranted hereon all changes and modifications as reasonably and properly come within the scope of their contribution to the art.

What is claimed is:

1. Acoustic therapy apparatus comprising a source of therapeutic acoustic waves and an ultrasound locating system with an ultrasound transducer, said source and the ultrasound transducer being combined to form an oblong applicator with a proximal end and a distal end with a longitudinal axis proceeding therebetween, the source and the ultrasound transducer being successively arranged in the direction of the longitudinal axis with said ultrasound transducer disposed at said distal end of said applicator, said ultrasound locating system generating ultrasound images with respect to a planar circular sector that contains the longitudinal axis of the applicator and whose center axis is the angle bisector of the plane and comprising means for adjusting the center axis of the circular sector, said ultrasound transducer being disposed relative to said source so that, proceeding from a position wherein the center axis of the circular sector describes an angle of less than 90° with a section of the longitudinal axis of the applicator located in the source in such a way, with the center axis of the circular sector being inclined toward the source, the center axis of the circular sector being adjustable by said means for adjusting such that said center axis forms an angle greater than 90° with said section of the longitudinal axis of the applicator located in the source.

2. Acoustic therapy apparatus according to claim 1, wherein said applicator comprises dimensions allowing said applicator to be introducible into the path body interior of a human patient on a natural path.

3. Acoustic therapy apparatus according to claim 1 when said source of therapeutic acoustic waves comprises an ultrasound source.

4. Acoustic therapy apparatus according to claim 3 wherein said ultrasound source has an elongated shape.

5. Acoustic therapy apparatus according to claim 4 wherein said ultrasound source comprises a linear array of transducer elements.

* * * * *